(12) United States Patent
Wu et al.

(10) Patent No.: US 9,068,921 B2
(45) Date of Patent: Jun. 30, 2015

(54) ANALYZER AND METHOD FOR SENSING USING THE SAME

(75) Inventors: Wei Wu, Palo Alto, CA (US); Qiangfei Xia, Sunnyvale, CA (US); Shih-Yuan Wang, Palo Alto, CA (US); Jingjing Li, Sunnyvale, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 896 days.

(21) Appl. No.: 13/254,883

(22) PCT Filed: Mar. 7, 2009

(86) PCT No.: PCT/US2009/036440
§ 371 (c)(1),
(2), (4) Date: Sep. 6, 2011

(87) PCT Pub. No.: WO2010/104497
PCT Pub. Date: Sep. 16, 2010

(65) Prior Publication Data
US 2011/0315902 A1 Dec. 29, 2011

(51) Int. Cl.
*G01N 21/01* (2006.01)
*G01N 21/05* (2006.01)
(Continued)

(52) U.S. Cl.
CPC .......... *G01N 21/05* (2013.01); *B01L 3/502715* (2013.01); *B01L 2200/0647* (2013.01);
(Continued)

(58) Field of Classification Search
CPC ... G01N 21/05; G01N 21/03; G01N 21/0303; G01N 21/31; G01N 21/314; G01N 2021/6467; G01N 2021/058; G01N 2021/0346; G01N 2021/3125; G01N 2021/3133; G01N 2021/3166; G01N 2201/08; B01L 2200/0647; B01L 2300/0851; B01L 2300/0864; B01L 2300/0867; B01L 2300/0896; B01L 2300/0861; B01L 2400/049; B01L 2400/0487; B01L 3/502715; B01L 3/502707; B01L 3/5027; B01L 3/502; B01L 3/50
USPC ............. 250/573–576, 428, 432 R, 435–437; 382/12; 435/287.1, 288.7; 422/502, 422/503
See application file for complete search history.

(56) References Cited

U.S. PATENT DOCUMENTS 5,726,751 A * 3/1998 Altendorf et al. ............. 356/246
5,923,481 A * 7/1999 Skidmore et al. ............. 359/819
(Continued)

FOREIGN PATENT DOCUMENTS

EP    1936382    6/2008
JP    2005221327    8/2005
(Continued)

OTHER PUBLICATIONS

Gramotnev, et al. "Single-Mode Sub-Wavelength Waveguide with Channel Plasmon-Polaritions in Triangular Grooves on a Metal Surface", Appl Phys Letters 85,6323 (2004).
(Continued)

*Primary Examiner* — John Lee
(74) *Attorney, Agent, or Firm* — Dierker & Associates, P.C.

(57) ABSTRACT

An analyzer is disclosed herein. The analyzer encompasses a substrate having a surface with a plurality of distinct V-grooves formed therein. An input flow channel is configured to intersect and fluidly communicate with each of the plurality of distinct V-grooves at respective input points, and an output flow channel is configured to intersect and fluidly communicate with each of the plurality of distinct V-grooves at respective output points.

15 Claims, 2 Drawing Sheets

(51) Int. Cl.
*B01L 3/00* (2006.01)
*G01N 21/03* (2006.01)
*G01N 21/31* (2006.01)
*G01N 21/64* (2006.01)

(52) U.S. Cl.
CPC .. *B01L2300/0851* (2013.01); *B01L 2300/0864* (2013.01); *B01L 2300/0867* (2013.01); *B01L 2300/0896* (2013.01); *B01L 2400/0487* (2013.01); *B01L 2400/049* (2013.01); *G01N 21/0303* (2013.01); *G01N 21/31* (2013.01); *G01N 2021/3133* (2013.01); *G01N 2021/3166* (2013.01); *G01N 2021/6467* (2013.01); *G01N 2201/08* (2013.01); *G01N 2021/0346* (2013.01)

(56) References Cited

U.S. PATENT DOCUMENTS

| | | | |
|---|---|---|---|
| 6,341,185 B1 | 1/2002 | Elster et al. | |
| 6,696,286 B1 | 2/2004 | Halverson | |
| 6,701,032 B1 | 3/2004 | Freeman | |
| 6,818,184 B2 * | 11/2004 | Fulwyler et al. | 422/68.1 |
| 7,005,292 B2 * | 2/2006 | Wilding et al. | 435/287.1 |
| 7,018,830 B2 * | 3/2006 | Wilding et al. | 435/287.1 |
| 7,019,831 B2 * | 3/2006 | Grossman et al. | 356/318 |
| 7,067,263 B2 * | 6/2006 | Parce et al. | 435/7.2 |
| 7,164,812 B2 | 1/2007 | Depeursinge et al. | |
| 7,245,379 B2 | 7/2007 | Schwabe | |
| 7,399,643 B2 | 7/2008 | Moon et al. | |
| 7,477,384 B2 | 1/2009 | Schwabe | |
| 7,763,856 B2 * | 7/2010 | Kiesel et al. | 250/343 |
| 7,952,705 B2 * | 5/2011 | Shen et al. | 356/246 |
| 8,221,700 B2 * | 7/2012 | Steinmiller et al. | 422/503 |
| 8,361,414 B2 * | 1/2013 | Akechi et al. | 422/503 |
| 8,480,975 B2 * | 7/2013 | Steinmiller et al. | 422/503 |
| 2002/0001695 A1 * | 1/2002 | Tajima et al. | 428/138 |
| 2002/0024662 A1 | 2/2002 | Ueno et al. | |
| 2002/0181837 A1 * | 12/2002 | Wang et al. | 385/16 |
| 2003/0118486 A1 * | 6/2003 | Zhou et al. | 422/102 |
| 2003/0129654 A1 * | 7/2003 | Ravkin et al. | 435/7.1 |
| 2003/0138969 A1 * | 7/2003 | Jakobsen et al. | 436/180 |
| 2003/0235905 A1 * | 12/2003 | Spiecker | 435/287.1 |
| 2004/0080744 A1 | 4/2004 | Hobbs | |
| 2004/0132205 A1 * | 7/2004 | Moon et al. | 436/174 |
| 2005/0140972 A1 | 6/2005 | Park | |
| 2006/0094119 A1 * | 5/2006 | Ismagilov et al. | 436/53 |
| 2006/0160208 A1 | 7/2006 | Putnam et al. | |
| 2006/0227328 A1 * | 10/2006 | Vanwiggeren et al. | 356/445 |
| 2007/0211985 A1 | 9/2007 | Duer | |
| 2007/0298433 A1 * | 12/2007 | Sia et al. | 435/7.1 |
| 2008/0038839 A1 * | 2/2008 | Linder et al. | 436/501 |
| 2009/0084496 A1 * | 4/2009 | Fonverne et al. | 156/292 |
| 2010/0072278 A1 * | 3/2010 | Putnam et al. | 235/454 |
| 2010/0172610 A1 * | 7/2010 | Gates et al. | 385/14 |
| 2010/0196207 A1 * | 8/2010 | Steinmiller et al. | 422/82.09 |
| 2011/0315902 A1 * | 12/2011 | Wu et al. | 250/576 |
| 2013/0252321 A1 * | 9/2013 | Steinmiller et al. | 435/287.2 |

FOREIGN PATENT DOCUMENTS

| | | |
|---|---|---|
| JP | 2006-053078 | 2/2006 |
| JP | 2007-113979 | 5/2007 |
| JP | 2008-070322 | 3/2008 |
| TW | 200844525 A | 11/2008 |

OTHER PUBLICATIONS

Malic et al: Integrated miniaturized optical detection platform for fluorescence and absorption spectroscopy Sensors and Actuators A, Elsevier Sequoia S.A Lausanne, CH. col. 135, No. 2, Apr. 4, 2007 pp. 515-524, XP022016214.

Supplementary European Search Report, Jul. 24, 2012, EP Patent Application No. 09841610.0, HPDC.

* cited by examiner

US 9,068,921 B2

ANALYZER AND METHOD FOR SENSING USING THE SAME

BACKGROUND

The present disclosure relates generally to an analyzer. Methods for sensing using the analyzer are also disclosed herein.

Assays and other sensing systems have been used in the chemical, biochemical, medical and environmental fields to detect the presence and/or concentration of one or more chemical substances. Recently, optical waveguides have been incorporated into such sensing systems. In some instances, the optical waveguides have been used for evanescent field production or to direct light in a desirable manner.

BRIEF DESCRIPTION OF THE DRAWINGS

Features and advantages of embodiments of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Embodiments of the analyzer disclosed herein advantageously integrate waveguides and fluidic channels into a single substrate, thereby providing a lab-on-a-chip sensor design. V-shaped grooves (also referred to herein as V-grooves), through which light is directed, are configured to coincide with a portion of the fluidic channels, and as such, fluid flows therethrough. The integration of the V-shaped grooves and the fluidic channels advantageously provides a substantial space for the light to interact with the fluidic sample(s). It is believed that the amount of light and fluid interaction that takes place within the analyzer advantageously results in plasmonic enhancement and increased signal output.

Furthermore, the analyzer may be configured with many different optical detection techniques, thereby enabling design versatility. For example, a single detection technique may be used, or multiple detection techniques may be integrated together in a single device.

The analyzer may also be used for a variety of sensing applications, including gas sensing, chemical sensing, biochemical or biological sensing, or the like.

Figure 1:
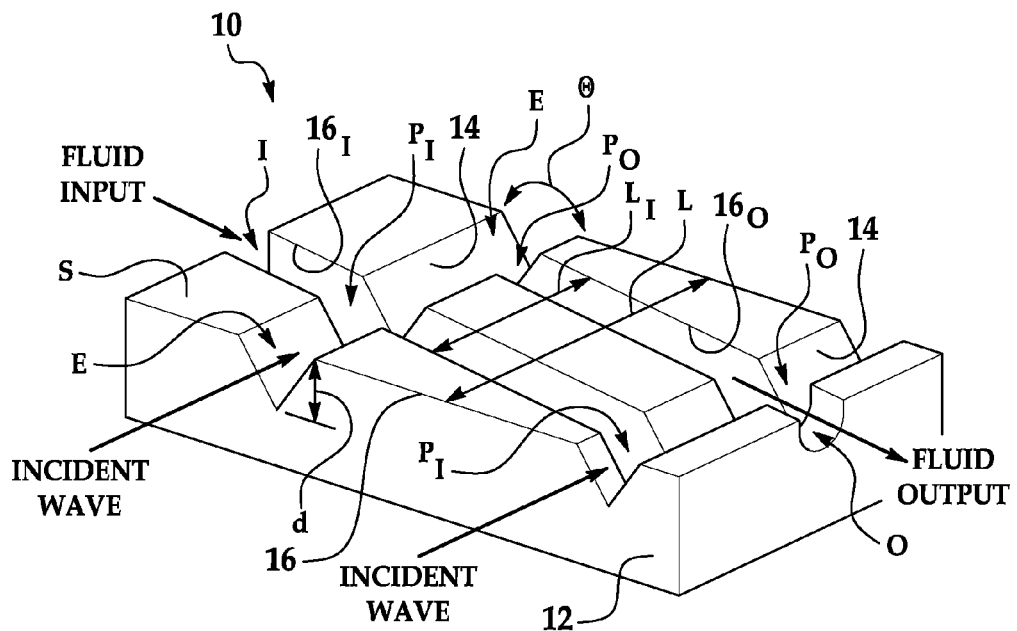
FIG. 1 is a semi-schematic perspective view of an embodiment of an analyzer including multiple V-grooves and multiple fluidic channels.

Referring now to FIG. 1, an embodiment of the analyzer 10 is depicted. The analyzer 10 includes a substrate 12 having V-grooves 14 and fluidic channels $16_I$, $16_O$ formed therein. The substrate 12 may be composed of any suitable material, including insulators (e.g., glass, quartz, ceramic (alumina), etc.), polymeric material(s) (e.g., polycarbonate, polyamide, acrylics, etc.), metals (e.g., Au, Ag, Ti, Pt, Pd, etc.), semiconductors (e.g., silicon, InP, GaAs, InAs, $In_xGa_{1-x}As_yP_{1-y}$ (where $0<x<1$, $0<y<1$)), silicon-on-insulator (SOI) substrates, or group III-V semiconductors on silicon on SOI substrates.

As shown in FIG. 1, multiple distinct V-grooves 14 are formed in the surface S of the substrate 12. The term "distinct V-grooves," as used herein, refers to separate V-shaped recesses that are formed in the substrate surface S, each of which is configured to be coupled to respective light sources and detectors (shown as reference numerals 18 and 20 in FIGS. 2 and 3). The V-grooves 14 may be substantially parallel to each other (as shown in FIG. 1), or may be positioned at any desirable angles with respect to one another, as long as the grooves 14 do not cross one another, and are in fluid communication with each of the fluidic channels $16_I$, $16_O$.

In one embodiment, the V-grooves 14 are formed in the substrate 12 via nanoimprint lithography, a thermal molding process, a hot embossing process, focused ion beam, photolithography, etching, or via ultraviolet (UV) imprinting. The angle θ and depth d of each V-groove 14 may vary, depending, at least in part, on the wavelength to be guided therethrough, the species to be detected, the type of signal to be detected, etc. In one non-limiting example, the groove angle θ ranges from near zero (e.g., greater than 0° and less than 1°) to about 60°, and the groove depth d ranges from about 100 nanometers to about 10 microns.

The length L of each of the V-grooves 14 may be equal to the length or width of the substrate 12, depending on the direction in which the V-grooves 14 are formed. If formed diagonally in the substrate 12, the length L of the V-grooves 14 will vary accordingly. In a non-limiting example, the length L of each of the V-grooves 14 ranges from about 100 nm (±1 nm) to about 1 mm (±0.25 mm). It is to be understood that the interaction length $L_I$ corresponds to the portion of the length L of the V-groove 14 where light introduced into the V-groove 14 interacts with fluid introduced into the V-groove 14. As such, the interaction length $L_I$ extends from an input point $P_I$ (i.e., the area at which the input channel $16_I$ and a respective V-groove 14 meet or intersect) to an output point $P_O$ (i.e., the area at which the output channel $16_O$ and a respective V-groove 14 meet or intersect).

When the substrate 12 is not formed of metal, it is to be understood that each of the V-grooves 14 may have a metal layer (not shown) established on each of its surfaces. In some instances, however, the metal layer may not be included. Non-limiting examples of metals that are suitable for the metal layer include silver or gold. When a separate metal layer is included in the V-grooves 14, the thickness of the layer generally ranges from about 5 nm to about 300 nm. Suitable deposition techniques for establishing the metal layer include evaporation, sputtering, and plating.

The V-grooves 14 may also be functionalized, depending, at least in part, on the sample to be analyzed via the analyzer 10. In an embodiment, the V-groove 14 surface may be functionalized with a receptor molecule, which binds with the molecule to be detected. For example, the V-groove 14 surface may be functionalized with a single strain of DNA, which complements the DNA sequence to be detected.

As previously mentioned, the substrate 12 also has fluidic channels $16_I$, $16_O$ formed therein. The fluidic channels $16_I$, $16_O$ may be formed via the same techniques used to form the V-grooves 14. The fluidic channels $16_I$, $16_O$ may also be fabricated at the same time as the V-grooves 14, or prior to or subsequent to fabrication of the V-grooves 14. The fluidic channels $16_I$, $16_O$ may have any desirable shape, including a V-shape, a rounded shape, a rectangular or square shape, or any other regular or non-regular geometric shape. In an embodiment, the fluidic channels $16_I$, $16_O$ have width and depth dimensions ranging from about 100 nanometers to about 1 millimeter.

It is to be understood that the analyzer 10 includes at least an input channel $16_I$ and an output channel $16_O$. The input channel $16_I$ has an inlet I that is configured to direct fluid into the analyzer 10 from a fluid source (not shown), and the output channel $16_O$ has an outlet O that is configured to direct fluid out of the analyzer 10 into, for example, a waste receptacle (also not shown). Both the input and output channels $16_I$, $16_O$ and are in fluid communication with each of the V-grooves 14.

"Fluid communication," as the term is used herein, means that fluid (e.g., gas and/or liquid) is able to freely move from the input channel $16_I$ into the V-grooves 14 and from each V-groove 14 into the output channel $16_O$. Fluid flows from the input channel $16_I$ into each V-groove 14 at respective input points $P_I$, and from each V-groove 14 into the output channel $16_O$ at respective output points $P_O$. It is to be understood that fluid flow may be active or passive. In one embodiment, positive pressure may be applied through the inlet I to push the fluid into the analyzer 10, negative pressure may be drawn from the outlet O to pull the fluid out of the analyzer 10, or both positive and negative pressure may be used to direct the fluid in a desirable direction through the analyzer 10.

Figure 2:
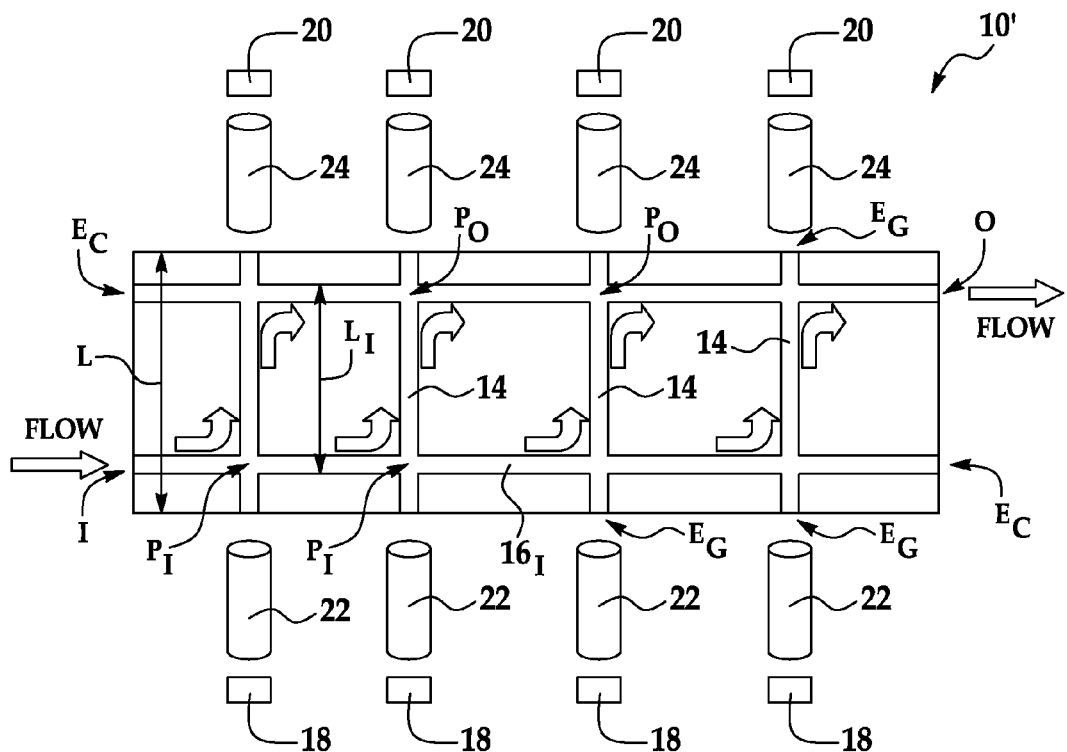
FIG. 2 is a schematic top view of another embodiment of the analyzer including multiple V-grooves, multiple fluidic channels, and multiple light input and output fibers.
Figure 3:
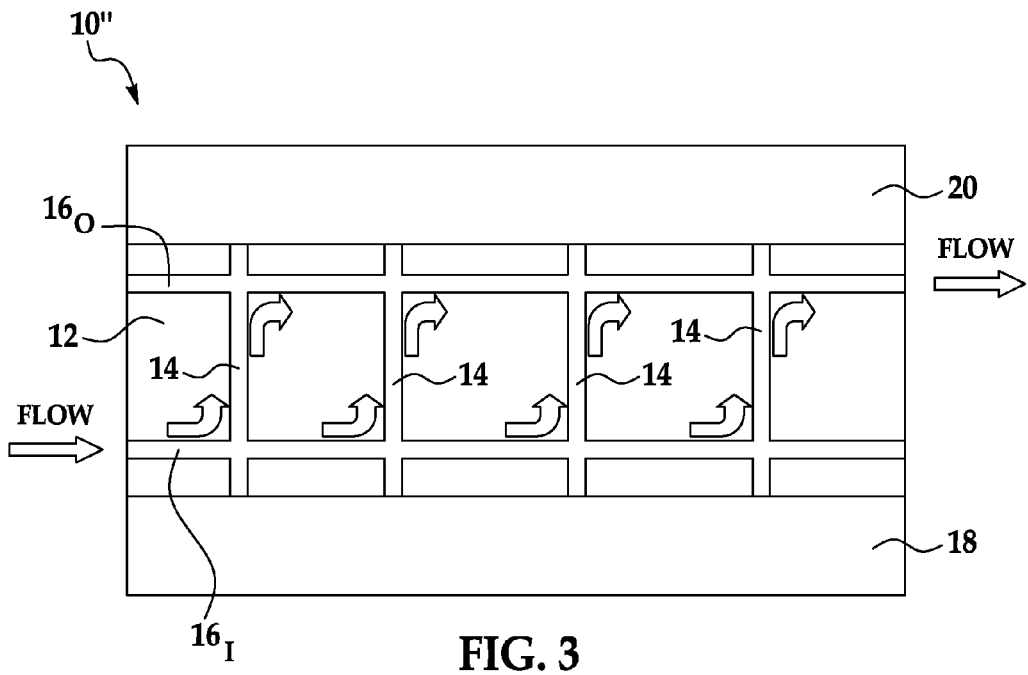
FIG. 3 is a schematic top view of still another embodiment of the analyzer including multiple V-grooves, multiple fluidic channels, and integrated light sources and detectors.

The fluid flow may be restricted at the ends $E_G$ of the V-grooves 14 by operatively positioning, at each end $E_G$, a stopping mechanism (not shown) that is transparent to the desirable wavelength transmitted through the V-groove 14 and to the optical signal that is generated. Examples of such stopping mechanisms include glass, silicon dioxide, or suitable polymers. In some instances, it may also be desirable to restrict fluid flow at ends $E_C$ (shown in FIGS. 2 and 3) of the channels $16_I$, $16_O$ as well. As shown in FIG. 1, the input channel $16_I$ begins at input I and ends at the second V-groove 14 (where the two form a T-shaped intersection), and the output channel $16_O$ begins at the first V-groove 14 (where the two form a T-shaped intersection) and ends at the output O. In such instances, no additional stopping mechanism is utilized to restrict fluid flow as it is desirable to have fluid flowing in via the input I and out via the output O. However, during manufacturing, it may be more desirable to construct the channels $16_I$, $16_O$ as they are shown in FIGS. 2 and 3, where both the input channel $16_I$ and the output channel $16_O$ are open at the ends $E_C$ that are opposed to the respective input I and output O. In such instances, a stopping mechanism may be secured to the substrate 12 or within the channels $16_I$, $16_O$ at these additional openings so that fluid does not exit the analyzer 10 at any point except at output O. The arrows in FIGS. 2 and 3 illustrate the fluid flow when such stopping mechanisms are incorporated into the analyzer 10.

While not shown in FIG. 1, it is to be understood that the embodiments of the analyzer 10 disclosed herein also include light sources 18 and detectors 20. One embodiment of the analyzer 10' including such components 18, 20 is shown in FIG. 2, and another embodiment of the analyzer 10" including such components is shown in FIG. 3.

Referring now specifically to FIG. 2, this embodiment of the analyzer 10' includes input fibers 22 (or any other optical mode in) and output fibers 24 (or any other optical mode out) which respectively guide light into a corresponding V-groove 14 and guide signals out of the corresponding V-groove 14. Each input fiber 22 (a non-limiting example of which is glass) is operatively connected to the corresponding V-groove at one of its two opposed ends, and to an individual light source 18. The input fiber 22 may not be physically connected to the V-groove 14 or the light source 18, but rather is positioned such that light from the light source is directed into the fiber 22, and then from the fiber 22 into the V-groove 14. In such instances, the core of the fiber 22 is aligned with the light source and the V-groove 14. In other embodiments, the input fiber 22 is physically connected to the V-groove 14.

Since each light source 18 is a source of light for a different V-groove 14, light of the same or different wavelengths may be introduced into each V-groove 14. The wavelength(s) of light selected for each V-groove 14 may depend, at least in part, on the samples to be analyzed, and the detection technique used with such V-groove. Non-limiting examples of suitable light sources 18 include lasers or light emitting diodes.

Similar to the configuration of the input fibers 22, each output fiber 24 is operatively connected to the other of the two opposed ends of the V-groove 14 (i.e., at an end opposite to the end adjacent to the input fiber 22). In some instances, the output fiber 24 (a non-limiting example of which is glass) may not be physically connected to the V-groove 14 or the corresponding detector 20, but rather is positioned such that signals from the V-groove 14 are directed into the fiber 24, and then from the fiber 24 to the detector 20. As such, the fiber 24 is aligned with the V-groove and the detector 20.

Since each detector 20 is associated with a different V-groove 14, the same or different detection techniques may be used in the same analyzer 10, 10'. The detector 20 selected for each V-groove 14 may depend, at least in part, on the samples to be analyzed, and the light directed into the V-groove 14. Non-limiting examples of suitable detectors 20 include photodetectors, which may be used alone or in combination with lenses and/or filters (e.g., wavelength dimension multiplex (WDM) filters). The spectroscopic detection techniques that may be utilized include Raman spectroscopy and advanced types of Raman spectroscopy (e.g., surface-enhanced Raman spectroscopy), IR spectroscopy, or photoluminescence.

As mentioned hereinabove, FIG. 3 illustrates yet another embodiment of the analyzer 10". In this embodiment, the light sources 18 and detectors 20 are integrated on the substrate 12, and thus are on-chip light sources 18 (e.g., on-chip lasers or photodiodes) and on-chip detectors 20 (e.g., on-chip photodetectors).

In all of the embodiments disclosed herein, a cover (not shown) may be established on the surface S in order to substantially enclose the channels $16_I$, $16_O$ and the V-grooves 14, such that light and fluid do not escape by undesirable means. The cover may be selected from the same materials as the substrate 12, and may be secured to the substrate 12 via wafer bonding.

Figure 4:
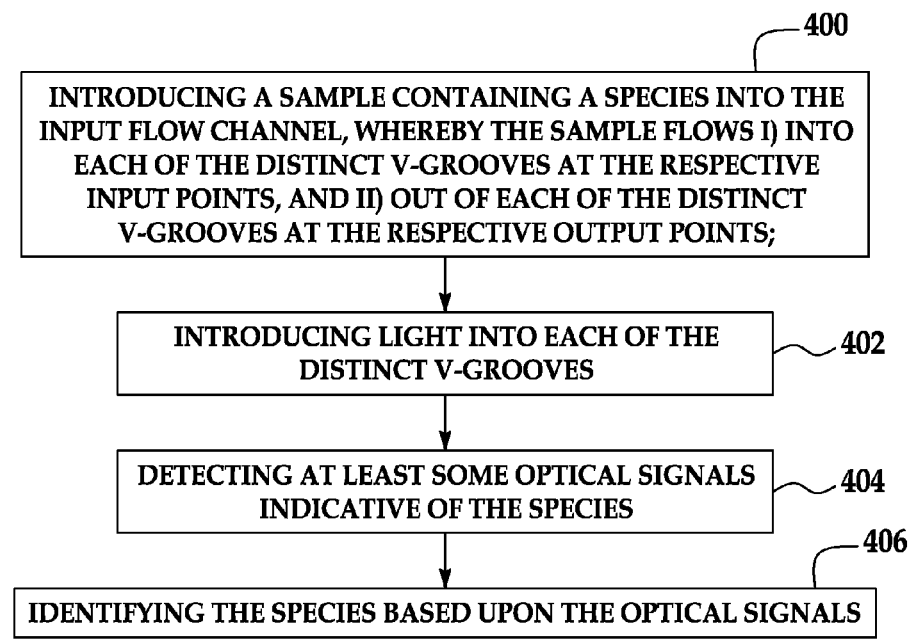
FIG. 4 is a flow diagram illustrating an embodiment of the method of using embodiments of the analyzer.

Referring now to FIG. 4, a method of using the analyzer 10, 10', 10" is depicted. The method generally includes introducing a sample containing a species into the input flow channel $16_I$, whereby the sample flows i) into each of the distinct V-grooves 14 at the respective input points $P_I$, and ii) out of each of the distinct V-grooves 14 at the respective output points $P_O$, as shown at reference numeral 400; introducing light into each of the distinct V-grooves 14, as shown at reference numeral 402; and detecting at least some optical signals indicative of the species, as shown at reference numeral 404. The method further includes identifying the species based upon the detected optical signals, as shown at reference numeral 406.

The sample that is introduced may be a gas or liquid that contains one or more unknown species (i.e., analyte) that is to be identified. The analyte may be molecules, compounds, cells, DNA, etc.

The sample is introduced into the analyzer 10, 10', 10" via the input I of the input flow channel 16$_I$. As the sample flows through the V-grooves 14, light is introduced from each of the light sources 18 into the corresponding V-grooves 14. The species within the respective V-grooves 14 will interact with the light therein, and such interaction generates optical signals that are guided out of the V-grooves 14 toward the respective detectors 20. The interaction of light with the species may be identified via a variety of different mechanisms (e.g., via a shift in the energy of the light photons, via absorption or transmittance of the light, via absorption and re-radiation of photons, etc.), and such mechanisms are detectable via appropriate detectors 20 (e.g., a Raman spectrometer, an IR spectrometer, a photoluminescence detector, etc.).

Since species interact differently from other species, the detected signals may be used to identify the species.

Since the V-grooves 14 are each distinct from the other V-grooves 14 in the analyzer 10, 10', 10", the light introduced into the respective V-grooves 14 may be the same or different. In one embodiment, each V-groove 14 has light of the same wavelength directed therein. This may be particularly suitable, for example, when i) the light directed into each V-groove 14 has a plurality of wavelengths across a wide spectrum, and each V-groove 14 is associated with a detector 20 configured to detect different wavelengths within the spectrum, or ii) each V-groove 14 is functionalized with a different receptor, or iii) Raman spectroscopy or photoluminescence (techniques in which a single incoming wavelength is needed) is used and the detectors 20 are configured to detect signals at different wavelengths.

In another embodiment, each V-groove 14 has light of a different wavelength directed therein. For example, one V-groove 14 may be associated with visible light, another V-groove 14 may be associated with infrared (IR) light, and still another V-groove 14 may be associated with ultraviolet (UV) light. In one example in which the analyzer 10, 10', 10" includes a few V-grooves 14, it may be desirable that each V-groove 14 be associated with a peak position (e.g., one V-groove 14 is associated with 700 nm, another V-groove 14 is associated with 750 nm, and still another V-groove is associated with 800 nm). In another example, it may be more desirable to include hundred(s) of V-grooves 14 (as opposed to a few). For example, one hundred and one parallel V-grooves 14 may be associated with respective single wavelengths that are 1 nm apart, such that the analyzer 10, 10', 10" functions as a spectrometer. In this example, the first V-groove 14 is associated with, for example, 700 nm wavelengths, an adjacent V-groove 14 is associated with, for example, 701 nm wavelengths, and the wavelength increases by 1 nm for each adjacent V-groove 14 until the last V-groove 14, which is associated with, for example, 800 nm wavelengths. These examples may be particularly suitable when it is desirable to detect a variety of different species, each of which interacts with a different wavelength of light, or a single species that interacts with multiple wavelengths of light.

In still another embodiment, each V-groove 14 has light of a variety of different wavelengths directed therein. For example, each V-groove 14 may have visible light, infrared (IR) light, and ultraviolet (UV) light directed therein. In such an embodiment, the generated optical signals would be demultiplexed upon exiting the V-grooves 14 and prior to being detected. This may be particularly suitable when it is desirable to detect one species that interacts with multiple wavelengths, or a multitude of different species that interact with different wavelengths. In one non-limiting example, this technique may be suitable when it is desirable to see the "peak" position instead of the strength, and thus it will be desirable to compare the signals from adjacent wavelengths. In another non-limiting example, this technique may be suitable when the signal from a single wavelength cannot provide enough information to identify the species of interest, and thus multiple wavelengths may be tested.

While several embodiments have been described in detail, it will be apparent to those skilled in the art that the disclosed embodiments may be modified. Therefore, the foregoing description is to be considered exemplary rather than limiting.

What is claimed is:

1. An analyzer, comprising:
    a substrate having a surface;
    a plurality of distinct V-grooves formed in the substrate surface, each of the V-grooves having two opposed ends and to carry a sample containing at least one species;
    an input flow channel configured to intersect and fluidly communicate with each of the plurality of distinct V-grooves at respective input points;
    an output flow channel configured to intersect and fluidly communicate with each of the plurality of distinct V-grooves at respective output points;
    a plurality of input fibers, each input fiber physically connected to one of the two opposed ends of a respective one of the plurality of distinct V-grooves, and each input fiber configured to direct light into the respective one of the plurality of distinct V-grooves; and
    a plurality of output fibers, each output fiber physically connected to an opposite of the two opposed ends of the respective one of the plurality of distinct V-grooves, and each output fiber configured to direct light out of the respective one of the plurality of distinct V-grooves.

2. The analyzer as defined in claim 1, further comprising a plurality of light sources, each light source operatively positioned to emit light into a respective one of the plurality of input fibers.

3. The analyzer as defined in claim 2 wherein a wavelength of light emitted from one of the plurality of light sources is different from a wavelength of light emitted from an other of the plurality of light sources.

4. The analyzer as defined in claim 2 wherein the plurality of light sources is operatively integrated with the substrate.

5. The analyzer as defined in claim 1, further comprising a metal layer established on each surface of each of the plurality of V-grooves.

6. The analyzer as defined in claim 1 wherein each of the plurality of input flow channels and each of the plurality of output flow channels is a microfluidic channel or a nanofluidic channel.

7. The analyzer as defined in claim 1, further comprising a plurality of detectors, each detector operatively positioned to detect light from a respective one of the V-grooves through its respective output fiber.

8. The analyzer as defined in claim 7 wherein the plurality of detectors is operatively integrated with the substrate.

9. The analyzer as defined in claim 1 wherein each V-groove has an interaction length extending between its input point and output point, and wherein the interaction length ranges from about 100 nm to about 1 mm.

10. A method for sensing the at least one species using the analyzer of claim 1, the method comprising:
    introducing the sample containing the at least one species into the input flow channel, whereby the sample flows i) into each of the distinct V-grooves at the respective input points, and ii) out of each of the distinct V-grooves at the respective output points;

introducing the light into each of the distinct V-grooves; and detecting at least some optical signals indicative of the at least one species.

11. The method as defined in claim 10 wherein the at least one species includes at least two species, wherein the light introduced into one of the distinct V-grooves has a wavelength that is different from a wavelength of the light introduced into an other of the distinct V-grooves, and wherein detecting includes:

detecting, via a first detector operatively positioned at an output of the one of the distinct V-grooves, optical signals indicative of one of the at least two species; and detecting, via a second detector operatively positioned at an output of the other of the distinct V-grooves, optical signals indicative of an other of the at least two species.

12. The method as defined in claim 10 wherein a wavelength of the light introduced into each of the distinct V-grooves is the same.

13. The method as defined in claim 10 wherein the at least one species includes one species, wherein the light introduced into one of the distinct V-grooves has a wavelength that is different from a wavelength of the light introduced into an other of the distinct V-grooves, and wherein detecting includes:

detecting, via detectors operatively positioned at an output of the one of the distinct V-grooves and at an output of the other of the distinct V-grooves, optical signals indicative of the one species.

14. The method as defined in claim 10, further comprising identifying the at least one species based upon the optical signals.

15. The analyzer as defined in claim 1, further comprising a cover secured to the substrate surface and substantially enclosing the plurality of input flow channels, the plurality of output flow channels, and the plurality of distinct V-grooves so that light and fluid are prohibited from escaping the analyzer through the cover.

\* \* \* \* \*